US011617573B2

(12) United States Patent
Comee et al.

(10) Patent No.: US 11,617,573 B2
(45) Date of Patent: Apr. 4, 2023

(54) DEVICES AND METHODS FOR SUTURING TISSUE

(71) Applicant: Boston Scientific Scimed Inc., Maple Grove, MN (US)

(72) Inventors: Shaun D. Comee, Fiskdale, MA (US); Peter L. Dayton, Brookline, MA (US); Ethan Miller, Ashland, MA (US); James J. Scutti, Norwell, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 398 days.

(21) Appl. No.: 17/009,949

(22) Filed: Sep. 2, 2020

(65) Prior Publication Data
US 2021/0068811 A1    Mar. 11, 2021

Related U.S. Application Data

(60) Provisional application No. 62/896,730, filed on Sep. 6, 2019.

(51) Int. Cl.
*A61B 17/04* (2006.01)
*A61B 1/00* (2006.01)
*A61B 1/018* (2006.01)
(Continued)

(52) U.S. Cl.
CPC ...... *A61B 17/0469* (2013.01); *A61B 1/00066* (2013.01); *A61B 1/018* (2013.01);
(Continued)

(58) Field of Classification Search
CPC ............ A61B 1/00066; A61B 1/00087; A61B 1/018; A61B 1/05; A61B 17/0469;
(Continued)

(56) References Cited

U.S. PATENT DOCUMENTS

| | | | | |
|---|---|---|---|---|
| 2002/0116011 | A1* | 8/2002 | Chee Chung | A61B 17/0469 606/145 |
| 2004/0138682 | A1* | 7/2004 | Onuki | A61B 17/0643 606/205 |

(Continued)

FOREIGN PATENT DOCUMENTS

EP    1345534 A1    9/2003

OTHER PUBLICATIONS

International Search Report and Written Opinion for the International Patent Application No. PCT/US2020/049002, dated Nov. 18, 2020, 24 pages.

*Primary Examiner* — Jocelin C Tanner
(74) *Attorney, Agent, or Firm* — Seager, Tufte & Wickhem, LLP

(57) ABSTRACT

The present disclosure relates generally to devices and methods for treating a tissue defect, for example, by suturing. In some embodiments, a suturing device may include an elongate member having a working channel, a suture channel, and a suture arm extending from the elongate member. The suturing device may further include a needle passer located within the working channel, the needle passer operable to deliver a needle between the elongate member and a distal end of the suture arm for suturing a target tissue, and a suture extending through the suture channel, wherein the suture is coupled to the needle. The suturing device may further include a plurality of imaging devices, wherein a first imaging device is positioned along a distal face of the elongate member, and wherein a second imaging device is positioned along the suture arm.

20 Claims, 5 Drawing Sheets

(51) Int. Cl.
  *A61B 1/05* (2006.01)
  *A61B 17/00* (2006.01)

(52) U.S. Cl.
  CPC ............ *A61B 1/05* (2013.01); *A61B 17/0482* (2013.01); *A61B 2017/0023* (2013.01); *A61B 2017/047* (2013.01); *A61B 2017/0477* (2013.01)

(58) Field of Classification Search
  CPC ............ A61B 17/0482; A61B 17/0625; A61B 90/361; A61B 2017/00017; A61B 2017/00115; A61B 2017/0023; A61B 2017/00296; A61B 2017/0034; A61B 2017/00349; A61B 2017/0477; A61B 2017/0609; A61B 2017/306; A61B 2090/0808; A61B 2090/371; A61B 2017/06052; A61B 2017/06009; A61B 17/0485; A61B 17/06004
  See application file for complete search history.

(56) References Cited

U.S. PATENT DOCUMENTS

| | | | |
|---|---|---|---|
| 2004/0158125 A1* | 8/2004 | Aznoian | A61B 17/0469 600/156 |
| 2005/0090709 A1 | 4/2005 | Okada et al. | |
| 2006/0047289 A1* | 3/2006 | Fogel | A61B 17/0625 606/139 |
| 2006/0282091 A1 | 12/2006 | Shelton et al. | |
| 2007/0129735 A1* | 6/2007 | Filipi | A61B 17/0469 606/144 |
| 2008/0021274 A1 | 1/2008 | Bayer et al. | |
| 2009/0177031 A1 | 7/2009 | Surti et al. | |
| 2010/0057109 A1* | 3/2010 | Clerc | A61B 17/0469 606/144 |
| 2012/0271327 A1 | 10/2012 | West et al. | |
| 2016/0367311 A1 | 12/2016 | Gerrans | |
| 2018/0235604 A1* | 8/2018 | Comee | A61B 17/0482 |

* cited by examiner

300

```
┌─────────────────────────────────────────────────────┐
│ INSERTING A SUTURING DEVICE WITHIN A PATIENT, THE   │
│ SUTURING DEVICE INCLUDING AN ELONGATE MEMBER        │
│ HAVING A PLURALITY OF WORKING CHANNELS AND A        │
│ SUTURE CHANNEL, A SUTURE ARM EXTENDING FROM THE     │
│ ELONGATE MEMBER, A NEEDLE PASSER EXTENDING WITHIN   │
│ THE WORKING CHANNEL, THE NEEDLE PASSER OPERABLE TO  │── 301
│ DELIVER A NEEDLE TO A DISTAL END OF THE SUTURE ARM, │
│ AND A SUTURE EXTENDING THROUGH THE SUTURE CHANNEL,  │
│ WHEREIN THE SUTURE IS COUPLED TO THE NEEDLE         │
└─────────────────────────────────────────────────────┘
                          │
                          ▼
┌─────────────────────────────────────────────────────┐
│ VIEWING A TARGET TISSUE USING A PLURALITY OF        │
│ CAMERAS, WHEREIN A FIRST CAMERA OF THE PLURALITY    │
│ OF CAMERAS IS POSITIONED ALONG A DISTAL FACE OF     │── 303
│ THE ELONGATE MEMBER, WHEREIN A SECOND CAMERA OF     │
│ THE PLURALITY OF CAMERAS IS POSITIONED ALONG THE    │
│ SUTURE ARM                                          │
└─────────────────────────────────────────────────────┘
                          │
                          ▼
┌─────────────────────────────────────────────────────┐
│ ENGAGING THE TARGET TISSUE USING A TISSUE           │
│ ACQUISITION DEVICE EXTENDING THROUGH A SECOND       │── 305
│ WORKING CHANNEL OF THE ELONGATE MEMBER              │
└─────────────────────────────────────────────────────┘
                          │
                          ▼
┌─────────────────────────────────────────────────────┐
│ ENGAGING THE TARGET TISSUE WITH THE NEEDLE          │── 307
└─────────────────────────────────────────────────────┘
```

*FIG. 7*

DEVICES AND METHODS FOR SUTURING TISSUE

CROSS-REFERENCE TO RELATED APPLICATION

The present application claims the benefit of priority under 35 U.S.C. § 119 to U.S. Provisional Patent Application 62/896,730, filed Sep. 6, 2019, which applications is incorporated herein by reference in its entirety for all purposes.

FIELD

The present disclosure relates to the treatment of tissue defects and, more particularly, to systems, devices, and methods for suturing tissue.

BACKGROUND

In some medical procedures, it is beneficial to fixedly connect a portion of tissue to another portion of tissue. Attaching portions of tissue, such as to hold together a wound or damaged tissue, with one or more sutures may allow adhesions to form between the tissue portions so that the attachment remains after the sutures are absorbed or removed. Often, an assembly including a needle and a suture coupled to the needle is used to suture tissue together. Of the known devices and methods for endoscopically closing tissue defects, each has certain advantages and disadvantages.

SUMMARY

The present disclosure in its various embodiments relates generally to systems, suturing devices, and methods for single-use, disposable suturing, which integrates visualization and navigation capabilities of an endoscope with the ability to target, acquire, close, and secure tissue. In one or more embodiments, a suturing device may include an elongate member having a working channel and a suture channel, and a suture arm extending from the elongate member. The suturing device may further include a needle passer located within the working channel, the needle passer operable to deliver a needle between the elongate member and a distal end of the suture arm for suturing a target tissue, and a suture extending through the suture channel, wherein the suture is coupled to the needle. The suturing device may further include a plurality of imaging devices, wherein a first imaging device of the plurality of imaging devices is positioned along a distal face of the elongate member, and wherein a second imaging device of the plurality of imaging devices is positioned along the suture arm. In some embodiments, the second imaging device of the plurality of imaging devices is positioned along the distal end of the suture arm. In some embodiments, a third imaging device of the plurality of imaging devices is positioned along a central area of the suture arm. In some embodiments, the suturing device may include a fourth imaging device of the plurality of imaging devices is positioned along a distalmost surface of the distal end of the suture arm. In some embodiments, the suturing device of claim may further include a second working channel extending through the elongate member, wherein a tissue acquisition device is located within the second working channel, and wherein the tissue acquisition device is operable to engage the target tissue. In some embodiments, the suturing device of claim may further include a third working channel, a first pull channel, a second pull channel, and a third pull channel, wherein the first pull channel is positioned adjacent the working channel, wherein the second pull channel is positioned adjacent the second working channel, and wherein the third pull channel is positioned adjacent the third working channel. In some embodiments, the suturing device may further include a needle lock positioned within the distal end of the suture arm, the needle lock operable to secure the needle within the distal end of the suture arm. In some embodiments, the needle lock may include a plunger including a ball detent operable to physically contact the needle. In some embodiments, the suturing device may further include a sensor embedded within the distal end of the suture arm, the sensor operable to detect a position of the needle.

In one or more embodiments, an endoscopic medical device may include an elongate member having a plurality of working channels and a suture channel, a suture arm extending from the elongate member, and a needle passer within a first working channel of the plurality of working channels. The needle passer is operable to deliver a needle between the elongate member and a distal end of the suture arm for suturing a target tissue. The endoscopic medical device may further include a suture extending through the suture channel, wherein the suture is coupled to the needle. The endoscopic medical device may further include a plurality of imaging devices, wherein a first imaging device of the plurality of imaging devices is positioned along a distal face of the elongate member, and wherein a second imaging device of the plurality of imaging devices is positioned along the suture arm. In some embodiments, the second camera of the plurality of cameras is positioned along the distal end of the suture arm. In some embodiments, the system may further include a second working channel of the plurality of working channels, wherein a tissue acquisition device is located within the second working channel, and wherein the tissue acquisition device is operable to engage the target tissue. In some embodiments, the endoscopic medical device may further include a third working channel, a first pull channel, a second pull channel, and a third pull channel, wherein the first pull channel is positioned adjacent the working channel, wherein the second pull channel is positioned adjacent the second working channel, and wherein the third pull channel is positioned adjacent the third working channel. In some embodiments, the elongate member has a substantially triangular cross-section, wherein the first pull channel and the working channel are positioned at a first angle defined by the triangular cross-section, wherein the second pull channel and the second working channel are positioned at a second angle defined by the triangular cross-section, and wherein the third pull channel and the third working channel are positioned at a third angle defined by the triangular cross-section. In some embodiments, the endoscopic medical device further includes a handle coupled to the elongate member, the handle comprising a needle actuation device coupled to the needle and a tissue acquisition actuator coupled to the tissue acquisition device. In some embodiments, the endoscopic medical device may further include a needle lock positioned within the distal end of the suture arm, the needle lock operable to secure the needle in position within the distal end of the suture arm, and a sensor embedded within the distal end of the suture arm, the sensor operable to detect a position of the needle or the needle lock.

In one or more embodiments, a method may include inserting a suturing device within a patient, the suturing device including an elongate member having a plurality of working channels and a suture channel, a suture arm extending from the elongate member, a needle passer within a first working channel of the plurality of working channels, the needle passer operable to deliver a needle to a distal end of the suture arm, and a suture extending through the suture channel, wherein the suture is coupled to the needle. The suturing device may further include a plurality of imaging devices, wherein a first imaging device of the plurality of imaging devices is positioned along a distal face of the elongate member, and wherein a second imaging device of the plurality of imaging devices is positioned along the suture arm. The method may further include engaging a target tissue with the needle. In some embodiments, the method may further include engaging the target tissue using a tissue acquisition device, the tissue acquisition device extending through a second working channel of the plurality of working channels. In some embodiments, the method may further include viewing the target tissue using the plurality of imaging devices, wherein the first imaging device and the second imaging device are positioned along different sides of the target tissue. In some embodiments, the method may further include securing the needle in position within the distal end of the suture arm using a needle lock, and detecting a position of the needle or the needle lock using a sensor embedded within the distal end of the suture arm.

Various one or more of the features summarized above may be interchanged, exchanged, combined or substituted with or for other features summarized above, for use in connection with the medical systems and methods summarized above, and with respect to the embodiments described in greater detail below and embodiments otherwise within the scope of the present disclosure.

BRIEF DESCRIPTION OF THE DRAWINGS

Non-limiting embodiments of the present disclosure are described by way of example with reference to the accompanying figures, which are not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. Furthermore, some of the figures include cross-sectional views in the form of "slices", or "near-sighted" cross-sectional views, omitting certain background lines or features otherwise visible in a "true" cross-sectional view, for illustrative clarity. In the figures:

FIG. 7 is a flow diagram of a method according to embodiments of the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

One trend in medicine includes moving from laparoscopic and open surgical procedures to miniaturized, endoscopic procedures. Endoscopists can perform ever more complex procedures noninvasively and under direct visualization. As a result, there exists a need for endoscopes possessing specific built-in treatment capabilities. Such scopes would facilitate both a broad range of procedural interventions more prevalent in hospitals, and further lead to the development of significantly more complex and capable scope designs.

Furthermore, infection prevention controls in the clinical setting create a demand for single-use scopes, which mitigate the risk of patient infection and associated adverse events. For example, currently commercial duodenoscopes are characterized by distal tips with complex mechanical features that are essential to the performance of the device. However, increased complexity also results in an inability to properly disinfect reusable scopes between procedures.

The disclosure pertains to medical devices, e.g., endoscopes, gastroscopes, bronchoscopes, colonoscopes, ureteroscopes, and the like, having integrated features for acquiring, manipulating, and closing openings in target tissue. Although single-use endoscopes are described herein, it is understood that embodiments of the present disclosure may be included in reusable medical devices such as endoscopes as well. Embodiments herein address at least the above deficiencies by integrating complex functions into a single endoscope. For example, the functions available according to the systems, suturing devices, and methods of the present disclosure may include one or more of the following: suturing, stapling, cutting, cauterizing, clip deployment, injection, tissue manipulation, and more.

Figure 1:
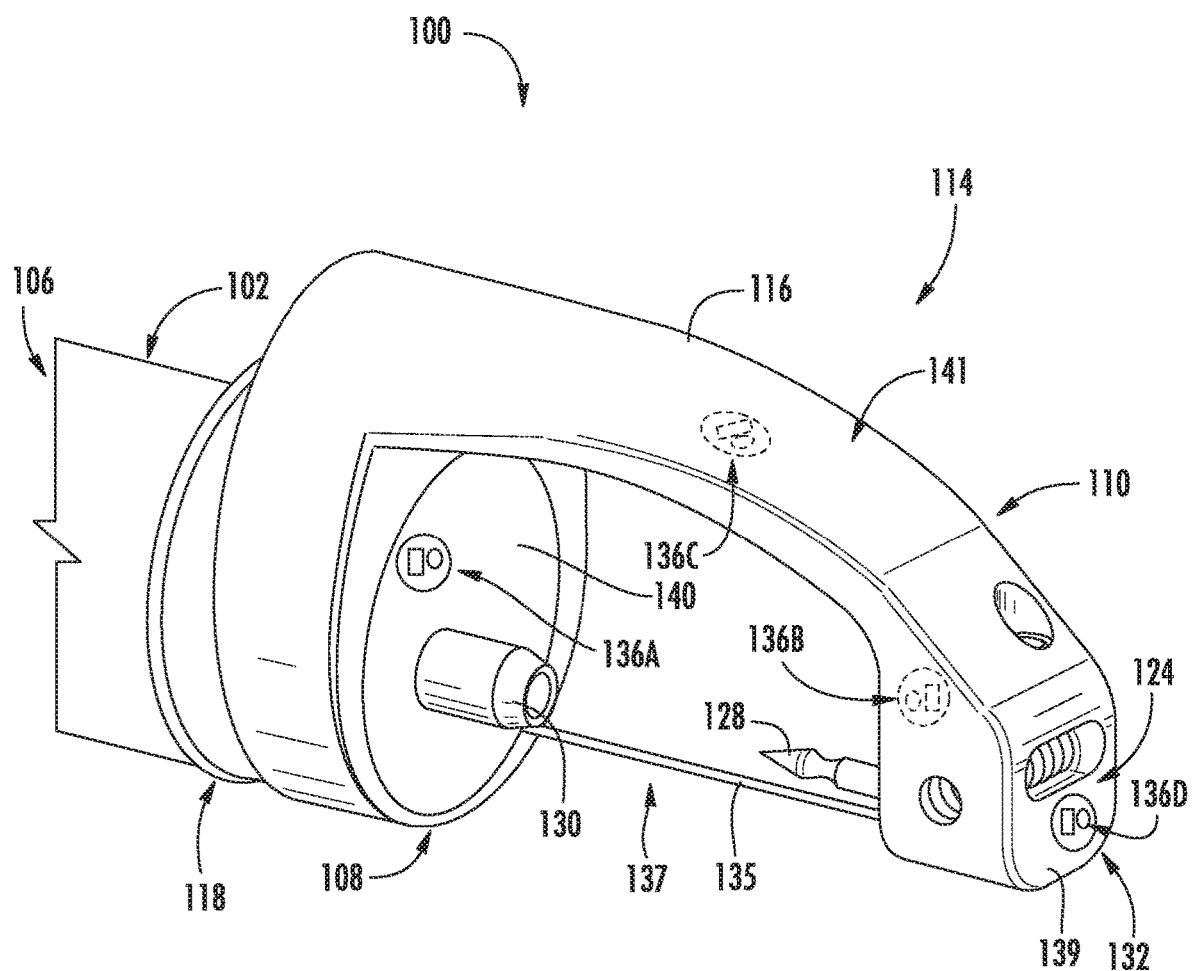
FIG. 1 is a perspective view of a portion a system according to embodiments of the present disclosure.

Turning now to FIG. 1, a suturing device, an endoscopic medical device, or system 100 according to embodiments of the disclosure will be described in greater detail. As shown, the system 100 may include an elongate member 102, such as a flexible hollow tube, endoscope, catheter, etc. The elongate member 102 may include a proximal end 106 opposite a distal end 108. In some embodiments, the elongate member 102 may be a flexible material, such as silicone, a thermoplastic elastomer including polyamide and polyether backbone blocks, polyurethane, etc., to allow for scope flexing. In other embodiments, the elongate member 102 may be a rigid material, such as polycarbonate, acrylonitrile butadiene styrene (ABS), etc., to provide a more direct positioning response.

The system 100 may further include a suture arm 110 extending from the distal end 108 of the elongate member 102. In some embodiments, the suture arm 110 may be part of a distal assembly 114 including a body 116 having a proximal section 118 extending from the distal end 108 of the elongate member 102. The proximal section 118 and the elongate member 102 may be integrally connected such that the distal assembly 114 and the elongate member 102 form an integrated, single use device. In other embodiments, the distal assembly 114 may be removably coupled to the elongate member 102.

As further shown, the suture arm 110 may extend to an endcap 124, which is configured to releasably engage and disengage a needle 128. In some embodiments, the needle 128 may be delivered by a needle passer 130 between the distal end 108 of the elongate member 102 and the endcap 124, which is located at a distal end 132 of the suture arm 110. The needle 128 may be connected to a suture 135 used for tensioning and closing an opening in a target tissue (not shown) retained within a suture cavity 137 defined by the suture arm 110.

In some embodiments, the system 100 may further include a plurality of imaging devices (e.g., cameras) 136A-136D surrounding the suture cavity 137. In embodiments, an illumination device may be disposed or positioned adjacent each imaging device 136A-136D. Advantageously, visualization of the target tissue is improved, thus allowing an operator of the system 100 to better recognize, during the procedure, correct passage of the needle 128 and suture 135, sufficient tensioning and closure of a target defect, cinching of the suture 135, etc. By providing the plurality of imaging devices 136A-136D located at different positions around the suture cavity 137, visual obstructions, for example, due to suturing tools within the suture cavity 137 and/or movement of the suture arm 110, may be mitigated.

For example, a first imaging device 136A may be positioned along a distal face 140 of the elongate member 102, while a second imaging device 136B may be positioned proximate the distal end 132 of the suture arm 110. For example, the second imaging device 136B may be secured to a surface of the endcap 124 facing the suture cavity 137. As such, the first and second imaging devices 136A-136B may be located on generally opposite sides of the target tissue. In some embodiments, the suture arm 110 may contain a third imaging device 136C positioned normal to a suturing plane, e.g., in a central area 141 of the suture arm 110, looking down at the target tissue. This third imaging device 136C may assist with evaluating the target tissue without needing to move or flex the system 100 to a position where the first and second imaging devices 136A-136B can visualize the target tissue.

It will be appreciated that more than three imaging devices may be present in other embodiments. For example, one or more additional imaging device 136D may be positioned along a distalmost surface 139 of the endcap 124 of the suture arm 110, facing away from the suture cavity, to provide an unobstructed view beyond the distal end 132 of the suture arm 110. In some embodiments, the operator may have the ability to switch between the different views provided by each the plurality of imaging devices 136A-136D, for example, using a button or similar mechanism on a user interface, such as an external monitor in communication with a handle of the system 100. It will be appreciated that the suture arm 110 may include any number of cameras, which can be used to combine the images into a single 180°, 270°, 360°, or surround view of the target tissue. In other embodiments, multiple images may be overlaid or stitched together to provide a 3-D or overall view of the suture cavity.

Figure 2:
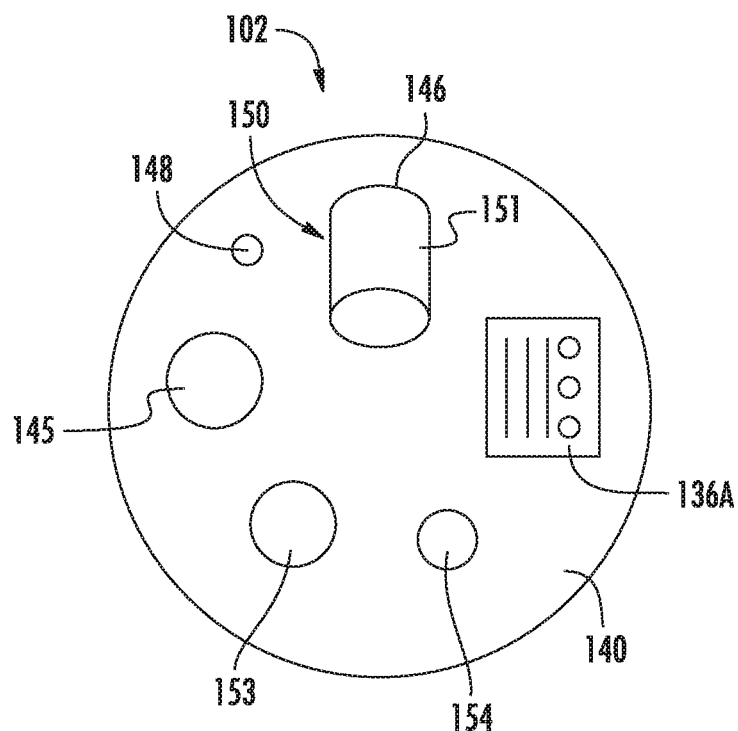
FIG. 2 is an end view of an elongate member of the system of FIG. 1 according to embodiments of the present disclosure.
Figure 3:
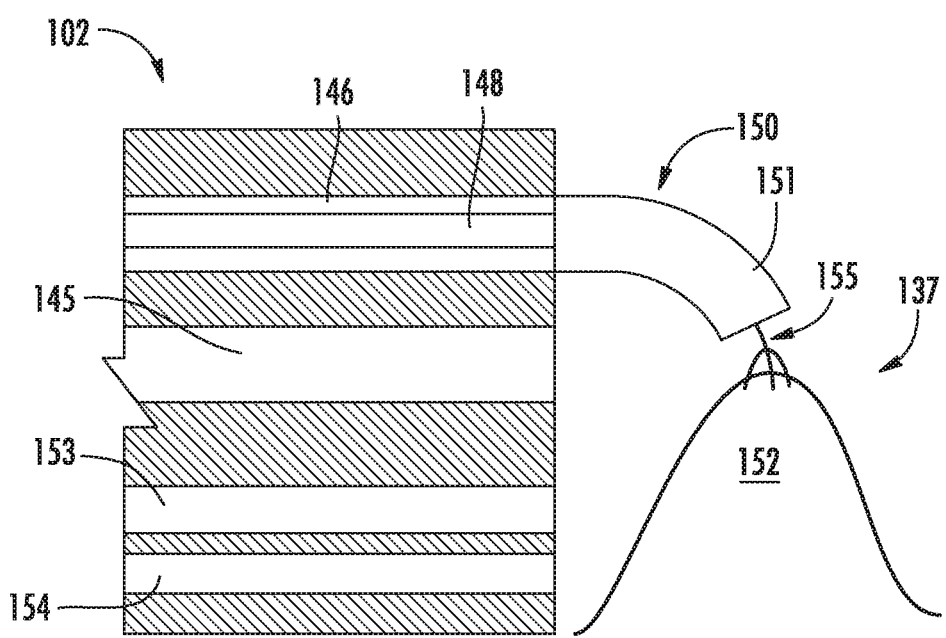
FIG. 3 is a side cross-sectional view of the elongate member of FIG. 2 according to embodiments of the present disclosure.

Turning now to FIGS. 2-3, the elongate member 102 according to embodiments of the present disclosure will be described in greater detail. As shown, the elongate member may include a plurality of channels extending therethrough, such as a first working channel 145, a second working channel 146, and a suture channel 148. In some embodiments, the first working channel 145 may contain the needle passer 130 (FIG. 1), while the second working channel 146 may contain a tissue acquisition device 150 operable to engage and bring a target tissue 152 into the suture cavity 137 (FIG. 1). The suture channel 148 may contain the suture 135 (FIG. 1). Separating the suture 135 from the needle passer 130 may be advantageous to avoid or reduce potential entanglement, when the suture 135 occupies the same channel as the main instrument, for example, when the suture wraps around a catheter. One or more additional channels may further be present, such as a suction channel 153 and a flush channel 154. Although two working channels and one suture channel are shown, it will be appreciated that there may be more or fewer channels in alternative embodiments. As further shown, the first imaging device 136A may be located along the distal face 140 of the elongate member 102.

Although non-limiting, the tissue acquisition device 150 may be a tissue grabber including a curved channel extension 151, and a hook or claw 155 (FIG. 3) extending from the curved channel extension 151. In other embodiments, the tissue acquisition device 150 may be helix device, wherein an exit of the second working channel 146 may be curved to angle the helix device towards the target tissue 152. In still other embodiments, the exit of the second working channel 146 may contain a mechanical device, such as an elevator, to bend or angle the helix device towards the target tissue 152 as the helix device exits the second working channel 146. The elevator is a mechanism used in some scopes, such as duodenoscopes, that enables an instrument to be bent and directed nearly perpendicular to the long axis of the scopes. In some embodiments, the tissue acquisition device 150 may be for applying suction to engage and position tissue as desired for suturing.

Figure 4:
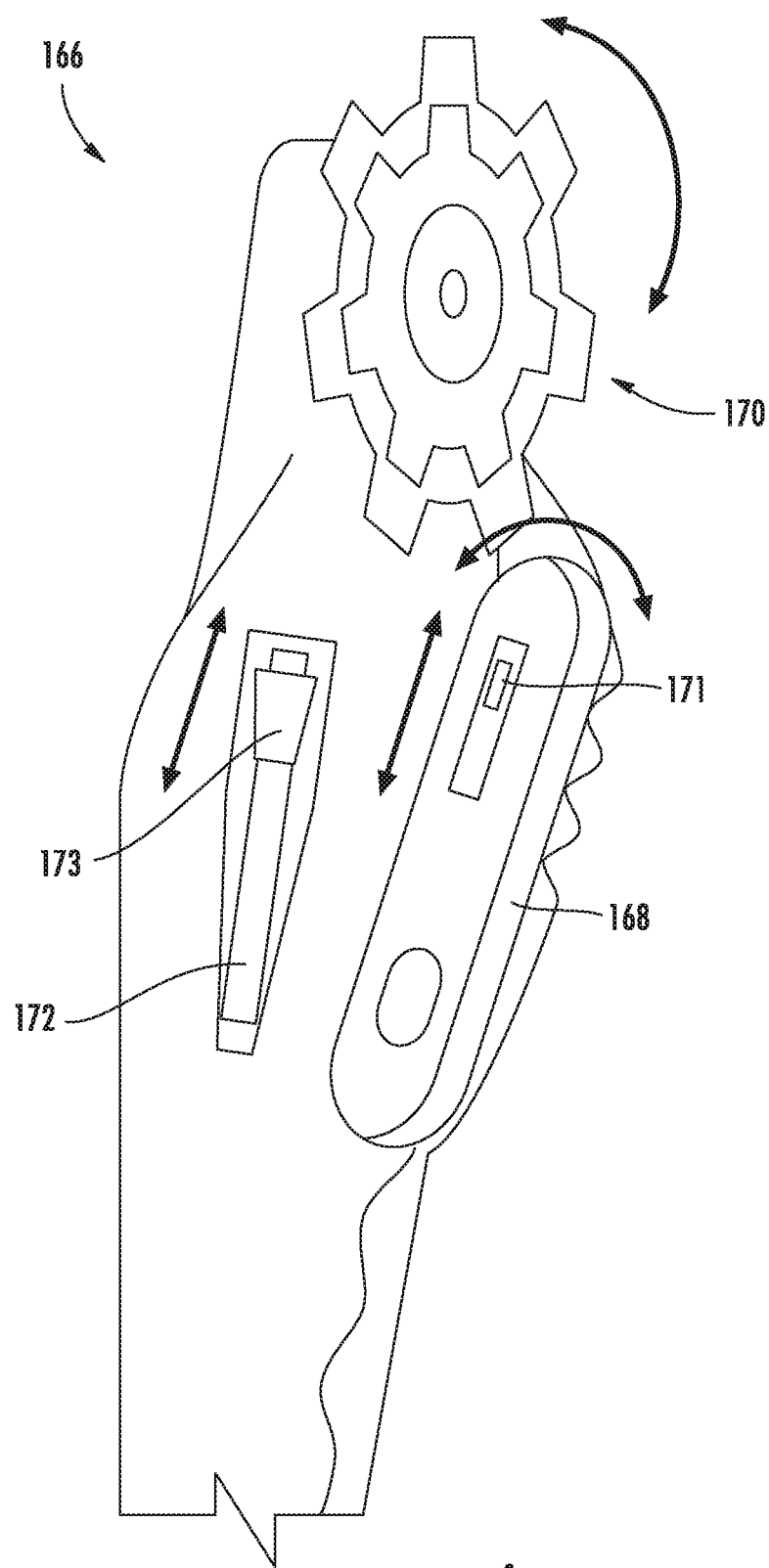
FIG. 4 depicts an example handle of the system according to embodiments of the present disclosure.

Turning now to FIG. 4, with reference also to the system 100 of FIG. 1, a handle 166 according to embodiments of the present disclosure will be described. Although not shown, the handle 166 may be operably coupled with the elongate member 102 of the system 100. The handle 166 represents a user interface for the operator of the system 100, and can be tailored to the functions the system 100 is performing. For example, the handle 166 incorporates distal steering functionality with tissue acquisition and needle passing capabilities. As shown, the handle 166 may include a needle actuation device 168 coupleable with the needle passer 130 and/or the suture 135, and one or more distal actuation knobs 170. Although non-limiting, the needle actuation device 168 may include a thumb slide 171 operable to move the needle 128 between the distal end 108 of the elongate member 102 and the endcap 124. In some embodiments, the needle actuation device 168 may be a rotatable lever for advancing and retracting the needle passer 130 within the first working channel 145. As further shown, the handle 166 may include a tissue acquisition actuator 172 coupleable with the tissue acquisition device 150. In this embodiment, the tissue acquisition actuator 172 may include a thumb slide 173.

In other embodiments, the tissue actuation actuator 172 may also include a device, such as a button or lever, to open and close the claw 155 of the tissue acquisition device 150. In some embodiments, the device may be integrated with the thumb slide 173. During use, an operator may move the thumb slide 173 down the handle 166 (i.e., away from the distal actuation knob 170), which advances the tissue acquisition device 150 distally toward the target tissue 152 (FIG. 3). Depressing the thumb slide 173 radially towards an interior of the handle 166 may then close the claw 155 of the tissue acquisition device 150 on the target tissue 155. While holding the thumb slide 173 in the depressed position, the thumb slide 173 may then be moved proximally or distally to manipulate the target tissue 155 as desired during suturing. Although not shown, it will be appreciated that the elongate member 102 may include multiple channels embedded therein to enable actuation wires, tubes, cables, extrusions, etc., to deliver movements applied at the handle 166 to each respective instrument (e.g., the needle passer 130, the tissue acquisition device 150, the suture 135, the needle lock 175, etc.) at the distal end of the system 100.

Advantageously, rather than the elongate member 102 providing means to pass devices, such as a separate device placed down the working channel of the scope, which takes time when switching between devices, the needle passer 130, the suture 135, and the tissue acquisition device 150 are integral to the system 100 and do not exit through various working channels. Instead, the needle passer 130, the suture 135, and the tissue acquisition device 150 terminate within the handle 160 itself, thus allowing the user to perform all functions independently, in an ergonomic and intuitive way.

Figure 5:
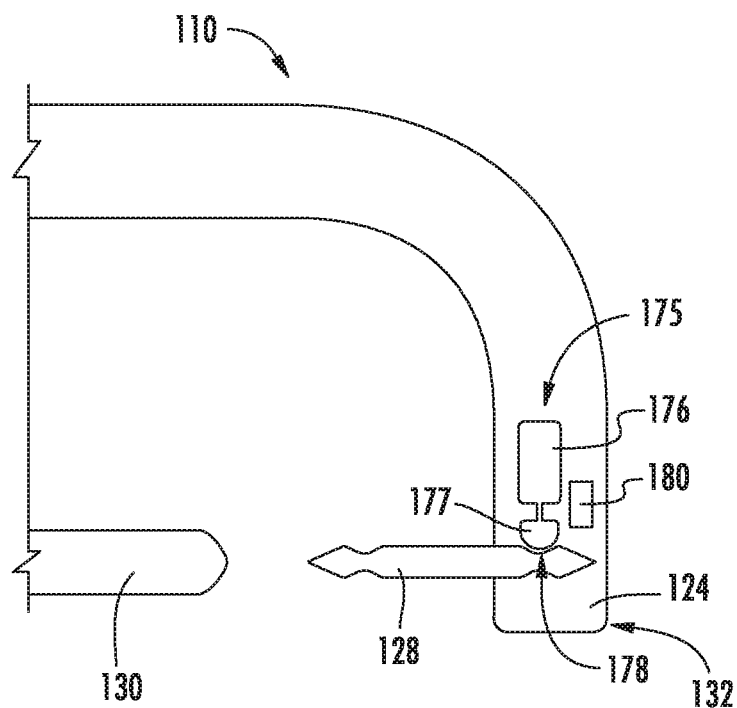
FIG. 5 is a side cross-sectional view of a suture arm of the system of FIG. 1 according to embodiments of the present disclosure.

FIG. 5 demonstrates the use of a needle lock 175 and a sensor 180 positioned within the distal end 132 of the suture arm 110 according to embodiments of the present disclosure. The needle lock 175 and sensor 180 may minimize unintentional dropped needles, providing tactile and/or visual feedback of needle retention. As shown, the needle lock may include a plunger 176 having a ball detent 177 operable to physically contact the needle 128 and secure the needle 128 in place. More specifically, the ball detent 177 may contact a groove 178 of the needle 128, preventing the needle 128 from moving towards the needle passer 130. In some embodiments, the plunger 176 may move vertically in a channel or slot (not shown) between a first, raised position and a second, lowered position. In the first position, the needle 128 is permitted to freely move in and out of the suture arm 110, and in the second position, the needle 128 abuts the ball detent 177, remaining fixed in position. Operation of the needle lock 175 may be controlled by the operator, for example, using the handle 166 shown in FIG. 4. In other embodiments, the needle lock 175 may be any passively actuated lock mechanism, e.g., a mechanism that does not require any user interface. Embodiments herein are not limited in this context.

As further shown, the suture arm 110 may contain one or more sensors 180 embedded within or secured thereto. To determine proper locking positioning of the needle lock 175, the sensor 180 may sense the presence or position of the needle lock 175, the needle 128, and/or a feature on the needle 128 for needle lock 175. The operator may then unlock the needle passer 130 from the needle 128 with confidence that the needle 128 will not drop. Additionally, the needle lock 175 may hold the needle 128 with sufficient force such that the needle 128 will not fall out of the endcap 124 if pushed on laterally. A higher force may be used because the operator does not need to overcome the retention force when retrieving the needle 128. Instead, the operator may have a button or similar mechanism on the user interface of the handle that sends a signal to release the needle 128. This enables the operator to unlock the needle 128 from the endcap 124 only when the operator is ready to retrieve it, preventing unintentional dropping of the needle 128.

In some embodiments, an output signal from the sensor 180 is used to generate feedback. Although non-limiting, the sensor 180 could be a proximity, magnetic, or impedance sensor with LED indicators (e.g., red, green lights) on the scope handle. Any combination of audio, visual, and tactile feedback signals may be generated to indicate locking and/or unlocking of the needle 128. In one embodiment, the handle may vibrate, indicating to the operator the needle 128 is in a locked arrangement. It will be appreciated that other feedback signals may be generated in alternative embodiments.

Figure 6:
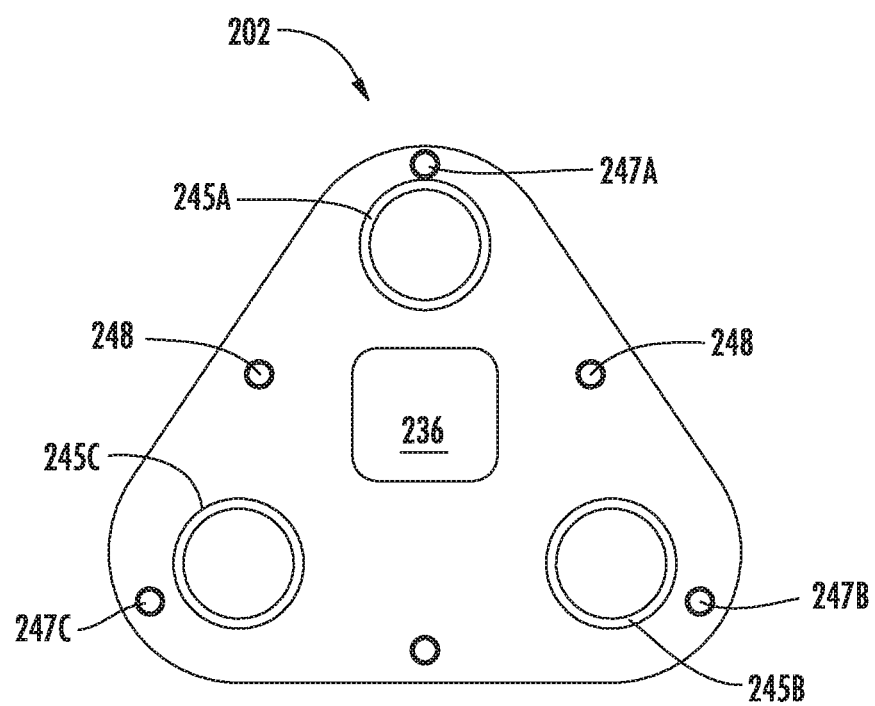
FIG. 6 is an end view of an alternative elongate member of the system of FIG. 1 according to embodiments of the present disclosure.

Turning now to FIG. 6, an embodiment of an elongate member 202 will be described. The elongate member 202 may be the same or similar in many aspects to the elongate member 102 described above. As such, only certain aspects of the elongate member 202 may be described hereinafter for the sake of brevity.

As shown, the elongate member 202 may have a substantially triangular cross-section, providing an alternative to more commonly used circular cross-section endoscopes. Advantageously, the triangular cross section provides a lower overall profile, yet with more usable volume for working channels and other internal components. For example, the elongate member 202 may include a first pull channel 247A and a first working channel 245A positioned at a first angle defined by the triangular cross-section, a second pull channel 247B and a second working channel 245B positioned at a second angle defined by the triangular cross-section, and a third pull channel 247C and a third working channel 245C positioned at a third angle defined by the triangular cross-section. In some embodiments, one or more additional pull channels 248 may be provided in the elongate member 202, for example, between the first, second, and/or third pull channels 247A-247C. The addition of more pull wires (not shown) may enhance the operator's ability to steer the elongate member 202 into a desired position by providing more fine-tuned movement capabilities. In some embodiments, the pull wires may terminate in the user interface via an analog interface including, for example, a joystick, ball, or other similar controller. Furthermore, the elongate member 202 may include one or more imaging devices and/or illumination devices (e.g., cameras) 236 positioned on a distal face 240 thereof.

FIG. 7 is a flow diagram of a method 300 according to embodiments of the present disclosure. At block 301, the method 300 may include inserting a suturing device within a patient, the suturing device including an elongate member having a plurality of working channels and a suture channel, a suture arm extending from the elongate member, a needle passer extending within the working channel, the needle passer operable to deliver a needle to a distal end of the suture arm, and a suture extending through the suture channel, wherein the suture is coupled to the needle.

At block 303, the method 300 may optionally include viewing a target tissue using a plurality of cameras, wherein a first camera of the plurality of cameras is positioned along a distal face of the elongate member, wherein a second camera of the plurality of cameras is positioned along the suture arm. In some embodiments, the first camera and the second camera are positioned along different sides of the target tissue. In some embodiments, additional cameras may be employed. For example, the suture arm may contain a third camera positioned normal to a suturing plane, e.g., in a central area of the suture arm, looking down at the target tissue. In other embodiments, a fourth imaging device may be positioned along a distalmost surface of the distal end of the suture arm.

At block 305, the method 300 may optionally include engaging the target tissue using a tissue acquisition device extending through a second working channel of the elongate member. In some embodiments, the tissue acquisition device may be a tissue grasper or a helix device.

At block 307, the method 300 may include engaging a target tissue with the needle. In some embodiments, the needle may pass through the target tissue multiple times, suturing the target tissue to repair an opening or tear, for example.

It will be appreciated that a variety of different materials may be used in forming the devices described herein. In some cases, a variety of different metals may be used. Illustrative but non-limiting examples of suitable metals include titanium, stainless steel, magnesium, cobalt chromium and others. In some embodiments, for example, the devices described herein may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), poly ulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Although non-limiting, as used herein with respect to the elongate member(s), the term "proximal portion" may refer to a portion of the endoscope closest to a handle or user interface of the system, while the term "distal end" may refer to a portion of the endoscope farthest from the handle or user interface of the system.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Still furthermore, although the illustrative method 300 is described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A suturing device, comprising:
an elongate member having a working channel and a suture channel;
a suture arm extending from the elongate member;
a needle passer located within the working channel, the needle passer operable to deliver a needle between the elongate member and a distal end of the suture arm for suturing a target tissue;
a suture extending through the suture channel, wherein the suture is coupled to the needle; and
a plurality of imaging devices, wherein a first imaging device of the plurality of imaging devices is positioned along a distal face of the elongate member, and wherein a second imaging device of the plurality of imaging devices is positioned along the suture arm.

2. The suturing device of claim 1, wherein the second imaging device of the plurality of imaging devices is positioned along the distal end of the suture arm.

3. The suturing device of claim 2, wherein a third imaging device of the plurality of imaging devices is positioned along a central area of the suture arm.

4. The suturing device of claim 2, wherein a fourth imaging device of the plurality of imaging devices is positioned along a distalmost surface of the distal end of the suture arm.

5. The suturing device of claim 1, further comprising a second working channel extending through the elongate member, wherein a tissue acquisition device is located within the second working channel, and wherein the tissue acquisition device is operable to engage the target tissue.

6. The suturing device of claim 5, further comprising a third working channel, a first pull channel, a second pull channel, and a third pull channel, wherein the first pull channel is positioned adjacent the working channel, wherein the second pull channel is positioned adjacent the second working channel, and wherein the third pull channel is positioned adjacent the third working channel.

7. The suturing device of claim 1, further comprising a needle lock positioned within the distal end of the suture arm, the needle lock operable to secure the needle within the distal end of the suture arm.

8. The suturing device of claim 7, wherein the needle lock comprises a plunger including a ball detent operable to physically contact the needle.

9. The suturing device of claim 7, further comprising a sensor embedded within the distal end of the suture arm, the sensor operable to detect a position of the needle.

10. An endoscopic medical device, comprising:
an elongate member having a plurality of working channels and a suture channel;
a suture arm extending from the elongate member;
a needle passer within a first working channel of the plurality of working channels, the needle passer operable to deliver a needle between the elongate member and a distal end of the suture arm for suturing a target tissue;
a suture extending through the suture channel, wherein the suture is coupled to the needle; and
a plurality of imaging devices, wherein a first imaging device of the plurality of imaging devices is positioned along a distal face of the elongate member, and wherein a second imaging device of the plurality of imaging devices is positioned along the suture arm.

11. The endoscopic medical device of claim 10, wherein the second imaging device of the plurality of imaging devices is positioned along the distal end of the suture arm.

12. The endoscopic medical device of claim 10, further comprising a second working channel of the plurality of working channels, wherein a tissue acquisition device is located within the second working channel, and wherein the tissue acquisition device is operable to engage the target tissue.

13. The endoscopic medical device of claim 12, further comprising a third working channel, a first pull channel, a second pull channel, and a third pull channel, wherein the first pull channel is positioned adjacent the working channel, wherein the second pull channel is positioned adjacent the second working channel, and wherein the third pull channel is positioned adjacent the third working channel.

14. The endoscopic medical device of claim 13, wherein the elongate member has a substantially triangular cross-section, wherein the first pull channel and the working channel are positioned at a first angle defined by the triangular cross-section, wherein the second pull channel and the second working channel are positioned at a second angle defined by the triangular cross-section, and wherein the third pull channel and the third working channel are positioned at a third angle defined by the triangular cross-section.

15. The endoscopic medical device of claim 12, further comprising a handle coupled to the elongate member, the handle comprising a needle actuation device coupled to the needle and a tissue acquisition actuator coupled to the tissue acquisition device.

16. The endoscopic medical device of claim 10, further comprising:
a needle lock positioned within the distal end of the suture arm, the needle lock operable to secure the needle in position within the distal end of the suture arm; and
a sensor embedded within the distal end of the suture arm, the sensor operable to detect a position of the needle.

17. A method, comprising:
inserting a suturing device within a patient, the suturing device comprising:
an elongate member having a plurality of working channels and a suture channel;
a suture arm extending from the elongate member;
a needle passer within a first working channel of the plurality of working channels, the needle passer operable to deliver a needle to a distal end of the suture arm;
a suture extending through the suture channel, wherein the suture is coupled to the needle; and
a plurality of imaging devices, wherein a first imaging device of the plurality of imaging devices is positioned along a distal face of the elongate member, and wherein a second imaging device of the plurality of imaging devices is positioned along the suture arm; and
suturing a target tissue using the needle.

18. The method of claim 17, further comprising engaging the target tissue using a tissue acquisition device, the tissue acquisition device extending through a second working channel of the plurality of working channels.

19. The method of claim 17, further comprising viewing the target tissue using the plurality of imaging devices, wherein the first imaging device and the second imaging device are positioned along different sides of the target tissue.

20. The method of claim 17, further comprising:
securing the needle in position within the distal end of the suture arm using a needle lock; and
detecting a position of the needle or the needle lock using a sensor embedded within the distal end of the suture arm.

* * * * *